United States Patent
Rudolph (10) Patent No.: US 11,806,546 B2
(45) Date of Patent: Nov. 7, 2023

(54) ARTIFICIAL INTELLIGENCE NEURO STIMULATION SYSTEM

(71) Applicant: Grant Rudolph, Mill Valley, CA (US)

(72) Inventor: Grant Rudolph, Mill Valley, CA (US)

(*) Notice: Subject to any disclaimer, the term of this patent is extended or adjusted under 35 U.S.C. 154(b) by 0 days.

(21) Appl. No.: 17/654,058

(22) Filed: Mar. 8, 2022

(65) Prior Publication Data

US 2022/0280800 A1 Sep. 8, 2022

Related U.S. Application Data (60) Provisional application No. 63/158,151, filed on Mar. 8, 2021.

(51) Int. Cl.
*A61N 1/00* (2006.01)
*A61N 2/00* (2006.01)
*G06N 5/022* (2023.01)

(52) U.S. Cl.
CPC .............. *A61N 2/006* (2013.01); *A61N 2/002* (2013.01); *G06N 5/022* (2013.01)

(58) Field of Classification Search
CPC ................................ A61N 2/002; A61N 2/006
See application file for complete search history.

(56) References Cited

U.S. PATENT DOCUMENTS

| | | | |
|---|---|---|---|
| 10,786,669 B2* | 9/2020 | Rajguru | A61N 2/006 |
| 2019/0255344 A1* | 8/2019 | Carter | A61N 1/36034 |
| 2022/0273961 A1* | 9/2022 | Riehl | A61N 2/02 |

* cited by examiner

*Primary Examiner* — Christine H Matthews
(74) *Attorney, Agent, or Firm* — Launchpad IP, Inc.; Christopher A. Wiklof (57) ABSTRACT

Advancements in Neurofeedback, Neuromodulation, Neuro-stimulation, Artificial Intelligence, Cognitive Learning Systems and Expert Systems defines a system and apparatus to assay neural brain activity and deliver neural stimulation based on natural and artificial intelligence. AINS embodiments provide the ability to treat mental dysfunctions and/or provide increased mental capacity. Embodiments measure brain activity and define a recommended neuro modulation/stimulation based on natural and artificial intelligence analysis.

14 Claims, 7 Drawing Sheets

ARTIFICIAL INTELLIGENCE NEURO STIMULATION SYSTEM

CROSS REFERENCE TO RELATED APPLICATIONS

The present application claims priority benefit from U.S. Provisional Patent Application No. 63/158,151, entitled "ARTIFICIAL INTELLIGENCE NEURO STIMULATION SYSTEM," filed Mar. 8, 2021, which, to the extent not inconsistent with the disclosure herein, is incorporated by reference.

SUMMARY

According to an embodiment, a neuro-stimulation system may be implemented to include a software application configured to run on a user electronic device, such as a cell phone. The software application and/or the user electronic device itself, when operated according to control provided by the software application, may be considered embodiments hereof. Other embodiments relate to server-based functions used to provide the software application to a user electronic device, provide therapeutic field modulation control schedules and parameters, and receive reports of user use of and response to the therapeutic field.

Embodiments relate to application of neuro-stimulation in non-clinical settings, including non-transitory computer readable data, methods applied in conjunction with operation of the non-transitory computer readable data, and, as indicated above, user electronic devices operative according to the non-transitory computer readable data.

According to embodiments, an Artificial Intelligence Neuro-stimulation System (AINS) includes an Artificial Intelligence (AI) analysis subsystem, either in an autonomous mode or as augmentation to Natural Intelligence (NI), drives a neuro-stimulation subsystem to provide personal dysfunction treatments and performance enhancement therapies. Optionally, the subsystems cooperate to allow neuro-stimulation to be self-administered. Typical treatments would have one practitioner address all issues pertaining to a person seeking treatment. The Artificial Intelligence Neuro-stimulation System (AINS) incorporates the Natural Intelligence of practitioners and specialists by instantiating this expertise into a NI expert computing environment. Furthermore the NI computing environment is augmented with an Artificial Intelligence computing environment that incorporates machine learning into the treatment methodologies and interaction with the Person Being Treated.

The subject matter Experts, Practitioners, Doctors and Specialists who have knowledge and expertise relating to the treatment of dysfunction, performance enhancement and or meditation may work with system and software engineers to develop backend system(s) and end user applications that address specific treatments. This process may define a personal questionnaire to begin assessment of the person seeking treatment. Additionally, knowledge and expertise by professionals is captured and managed by the Natural Intelligence expert systems and the Artificial Intelligence (AI) systems. Additional training of the AI systems may be performed by the professionals and by the body of information obtained by the treatment of the large user population. This system provides the capability for continuous improvement and real time modification for identified conditions.

According to embodiments, a system and apparatus may incorporate a multiplicity of wired or wireless Electrophysiological, Neuro-stimulation and Neurofeedback technologies into a headset that is worn by the person being treated. The Electrophysiological and Neuro-stimulation headset may be interfaced to a smartphone, which is a handheld computer with a multiplicity of connectivity.

The Electrophysiological and Neuro-stimulation headset may also include a peripheral nerve interface. A peripheral nerve interface is the bridge between the peripheral nervous system and a computer interface, which serves as a bidirectional information transducer, for recording and sending signals between the human body and a machine processor.

Interfaces to the nervous system may take the form of electrodes for electrical stimulation and recording, although chemical stimulation and sensing are possible. Peripheral nerve interfaces may enable electrical stimulation and recording of the peripheral nervous system to study the form and function of the peripheral nervous system.

The smartphone computing client may use a cell phone network (e.g., 3G, 4G, 5G), and or the IEEE 802.11 Wi-Fi to connect to an Internet based cloud computing center that has been configured to deliver the AINS services. The smartphone may have an AINS application or set of applications installed enabling the smartphone to interface with an Electrophysiological and Neuro-stimulation headset via Bluetooth or other wireless or wired interfaces.

The smartphone, Neuro-stimulation headset and related software applications provide a User eXperience (UX) (or User Interface) facilitating the person being treated to communicate the area of treatment, a current condition, and, with the Natural Intelligence (NI) and Artificial Intelligence (AI) virtual agent, self-administer the appropriate Neuro-stimulation(s).

According to embodiments, this entire process may be remotely monitored, via the AINS smartphone application by a connected remote Cloud Data Center that manages each session. Each specific type of treatment may be managed by the AI Systems based on user login authentication and subsequent personal profile data. This user acceptance procedure is analyzed by the Natural Intelligence (NI) and Artificial Intelligence (AI) systems agents that have been created and trained by industry professionals.

In the event that the AINS system is not able to obtain clear and consistent results from the user assessment and registration process that is required to create an account in the AINS system, that user may be denied admission. The AINS system may capture and record each event, as this will provide valuable real world evaluation and learning opportunities for the Natural and Artificial Intelligence systems employed to manage the entire user community.

Concurrent with these user-centric activities, a multiplicity of focus-oriented business/social media networks may be constructed. The preferred embodiment may include three classes of business and social media networks to enhance the publishing and exchange of information. These may include:

1. A System and Software Developer Professional Network,
2. a Practitioner, Subject Matter Expert and Doctor Professional Network, and
3. a User Social Media Network.

Each of these personal and professional media networks may allow the creation of specific areas of interest that facilitate the sharing of information, treatments, and individual experiences. Beyond the personal and professional users, the NI and AI systems may also be configured to ingest business and social media content for learning and evaluation. This process delivers constant improvement on an ongoing basis, while identifying areas of interest and treatment protocols that may be outside the scope of the AINS system designer's offerings.

Embodiments include end user hardware and software that connects to a cloud data center that delivers AI agent-based support for setup, operation and administration of Neuro-stimulation and neurofeedback based treatments. These activities include end user, professional and developer online communities.

According to an embodiment, a method for applying neuro-stimulation includes receiving, into a server computer via a graphical user interface of a user device, a condition identification corresponding to a condition experienced by a patient, wherein the condition is treatable by neuro-stimulation. The method may include reading, from a non-transitory computer-readable medium, a session neuro-stimulation schedule corresponding to the condition from a plurality of neuro-stimulation schedules corresponding to respective conditions, and outputting the session stimulation schedule from the server computer to the user device. In an embodiment, the method includes causing the user device to display a control graphical user interface. The method may include enabling the user device to control a neuro-stimulation headset for applying the session neuro-stimulation schedule.

DETAILED DESCRIPTION

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

Neurofeedback and neuro-stimulation devices and therapies may be designed and deployed for a variety of treatments. Disorders addressed include: developmental disorders, bipolar, depressive, anxiety, Attention Deficit Disorder (ADD), learning disorders, mood disorders, anxiety, depression, Obsessive-Compulsive Disorder (OCD), Post-Traumatic Stress Disorder (PTSD), Traumatic Brain Injury (TBI), chronic fatigue, migraines, fibromyalgia, pain management, seizures, phobias, cognitive decline, memory loss, eating, sleep and sexual disorders, disruptive, impulse and conduct disorders, addictive, neurocognitive and personality disorders.

Performance enhancement applications include accelerated learning, meditation, stress management, creativity, organization, productivity, energy regulation or stamina and physical performance.

Current approaches require a practitioner to analyze, prescribe and administer the neuro-stimulation. These sessions are typically 30-60 minutes in duration. Only a small portion of that time may be actual neuro-stimulation.

Embodiments disclosed herein incorporate technological approaches used in Electroencephalogram (EEG) applications. Electroencephalography is an electrophysiological monitoring method to record electrical activity on the surface of the brain.

Quantitative electroencephalography (qEEG) is an analysis of EEG data and associated behavioral correlates.

The terms neuro feedback (NFB), neurofeedback (NFB) neurotherapy and neurobiofeedback may be considered synonymous, unless context indicates otherwise. NFB is a type of biofeedback that may be visualized as a real-time display of brain activity via EEG. In some cases, NFB has been actualized as an approach to purportedly teach self-regulation of brain function. EEG sensors are placed on the scalp to measure activity. Traditional Neurofeedback frequency training provides visual or auditory cues when the brain enters or leaves a target frequency range. Neurofeedback also includes Z-score training, which compares the signals received to a database and scores their variation level from the data base average. Low Resolution Brain Electromagnetic Tomography (LORETA) may be considered to be akin to a three-dimensional variant of conventional EEG that is understood to image the electrical activity of the brain.

Reflective Neurofeedback is a type of neurofeedback in which the information returned to the Person Being Treated does not enter through the senses, such as watching a computer screen, but directly to the brain trans-cranially. The Person Being Treated does not see, hear or do anything. Reflective Neurofeedback is an information-rich form of stimulation.

The 10-20 system or International 10-20 system is an internationally recognized method that defines the location of scalp electrodes for EEG on humans.

Neuro-stimulation includes the purposeful modulation of the nervous system's activity using invasive microelectrodes or non-invasive means such as Reflective Neurofeedback, transcranial magnetic stimulation or transcranial electric stimulation (tES), Transcranial Direct Current Stimulation (tDCS), transcranial alternating current stimulation, [tACS], pulsed electromagnetic Stimulation (pEMF), or transcranial Random Noise Stimulation (tRNS). Neuro-stimulation has been studied with respect to providing either pink noise or white noise. Neuro-stimulation may be applied as a steady field or as a pulsed field. Neuro-stimulation may also include: transdermal neural photonic stimulation using a multiplicity of wavelengths, Low Level Light/Laser Therapy, Subsonic, Sonic, ultrasonic and vibration stimulation.

Expert systems are computer systems that emulate the decision-making ability of a human expert. Expert systems are designed to solve complex problems by reasoning about knowledge, represented mainly as if—then rules rather than through conventional procedural code. Expert Systems allow the ability to capture Natural Intelligence and deploy it with client server based computing models.

Artificial Intelligence, Machine Intelligence, Machine Learning and Cognitive Systems describe a body of computer science that allows the training and reasoning capabilities of humans to be instantiated into computing systems.

Cloud computing is an on-demand computing capability that leverages Internet based computing to share processing resources and data to computers and other devices on demand.

A smartphone is a handheld personal computer with an operating system and an integrated mobile broadband cellular network, Wi-Fi, Bluetooth and GPS connections for location, voice and data communication. Smartphones are able to run a variety of third-party software components ("apps") in the phone and connect to computing clouds.

Social Media Networks are computer-mediated technologies that facilitate the creation and sharing of information, ideas, career interests and other forms of expression via virtual communities and networks.

Figure 1:
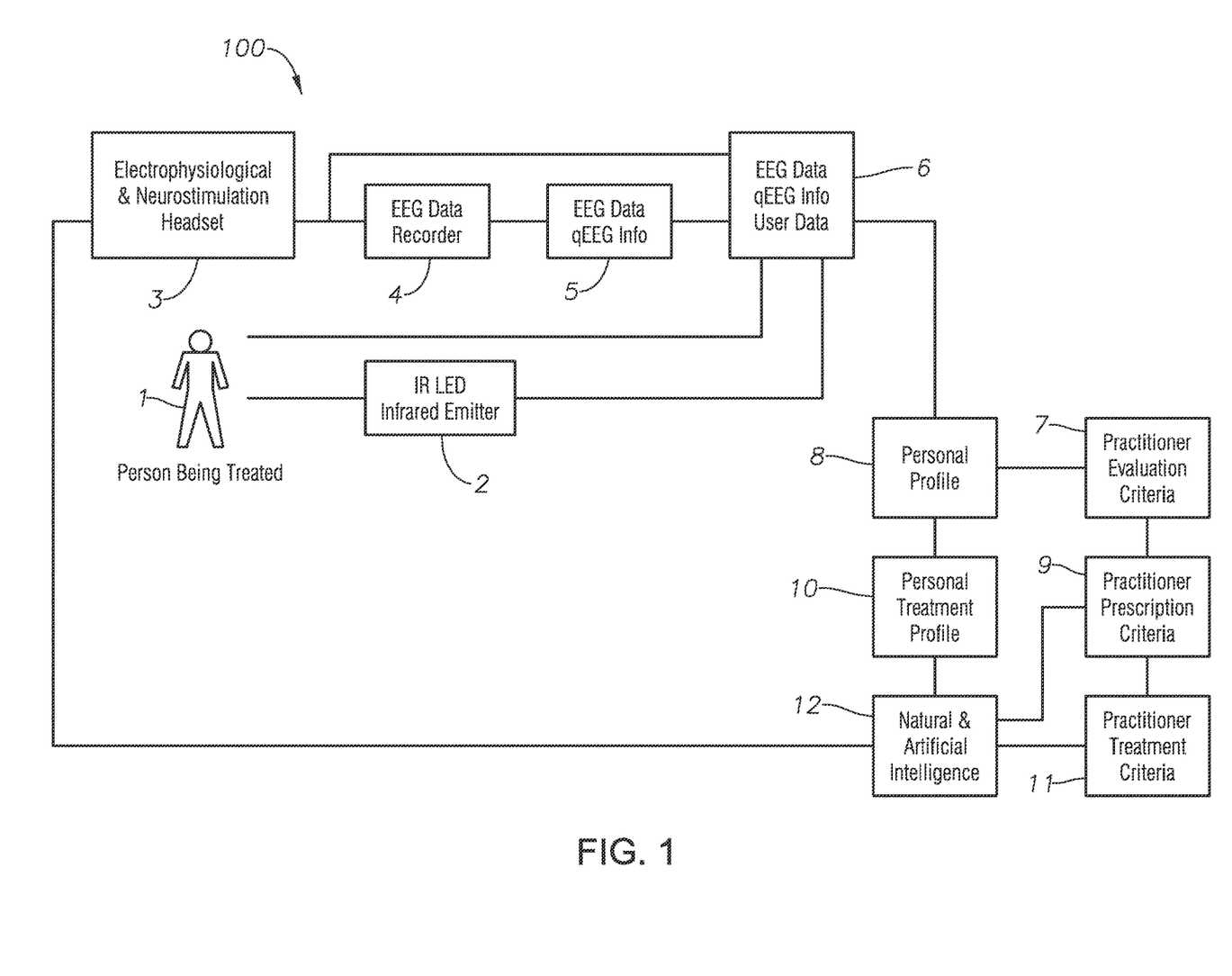
FIG. 1 is an Artificial Intelligence Neuro-stimulation System (AINS) Logical Diagram, according to an embodiment.

FIG. 1 is a Logical Diagram of an Artificial Intelligence Neuro-stimulation System (AINS) 100, according to an embodiment. The elements of the system are described below:

1). Person Being Treated is an individual that is seeking brainwave monitoring and Neuro-stimulation as an approach to address some mental dysfunction, attain a meditation state or enhance performance, both physical and mental.

2). IR LED Infrared Emitter is an Infrared Light Emitting Diode (LED) device emitting electromagnetic radiation between microwaves and red visible light in the electromagnetic spectrum, having frequencies between 300 gigahertz and 400 terahertz and wavelengths between 1 millimeter and 750 nanometers. This device is used to test the sensitivity of the Person Being Treated (1) to Infrared (IR) emissions.

3). Electrophysiological & Neuro-stimulation Headset is an apparatus constructed of detectors and emitters as required to measure brainwave and related physiological parameters of a Person Being Treated (1), and to stimulate selected portions of the brain of a Person Being Treated. The measurement of each individual's physiological parameters may help define the type, parameters and values of the appropriate neuro-stimulation/s.

4). EEG Data Recorder is a specially configured computer program that can digitize the received brainwave waveforms generated in the Electrophysiological & Neuro-stimulation Headset (3) by the Electroencephalogram (EEG) and record one or more channels over time. These recording create a permanent record of the Person Being Treated (1) brainwaves before, during and after Neuro-stimulation.

5). EEG Data to qEEG Information. Quantitative Electroencephalography (qEEG) is a procedure that processes the recorded EEG activity from a multi-electrode recording using a computer. This multi-channel EEG data is processed with various algorithms, such as the "Fourier" classically, or in more modern applications "Wavelet" analysis. The digital data is statistically analyzed, comparing values with "normative" database reference values managed by the Natural and Artificial Intelligence (12). The processed EEG is commonly converted into color maps of brain functioning called "Brain maps". These brain maps create permanent records of the Person Being Treated (1) brainwaves before, during and after Neuro-stimulation.

6). EEG Data, qEEG Info, User Data. The Person Being Treated (1) may undergo an assessment process for review by the Natural and Artificial Intelligence (12) to determine how to classify each individual. Some information is collected by the Person Being Treated (1) completing an online questioner, testing their ability to sense the IR LED Infrared Emitter (2) and recording EEG brainwaves (3) for processing into qEEG information (5) and other related biomarkers.

7). Practitioner Evaluation Criteria. Each individual may be classified by the Natural and Artificial Intelligence (12) by accessing the EEG Data, qEEG Info, User Data (6) stored in the Personal Profile (8) by the parameters and values established by the Practitioner Evaluation Criteria. This practitioner defined criteria may train and inform the Natural and Artificial Intelligence (12) as to acceptable classification and assessment management.

8). Personal Profile. Each Person seeking treatment and Person Being Treated (1) may undergo the assessment process and all the data collected may be become persistent in the individual's permanent record Personal Profile.

9). Practitioner Prescription Criteria. Once the Person seeking treatment has been successfully assessed by the Natural and Artificial Intelligence (12) and has become a Person Being Treated (1) the Practitioner Prescription Criteria may interact with other criteria in the Natural and Artificial Intelligence (12) to define a course of treatment.

10). Personal Treatment Profile. Each Person Being Treated (1) who has actually undergone treatment defined by the Natural and Artificial Intelligence (12) may have the specifics of before, during and after treatment permanently stored in the individuals Personal Treatment Profile. The Personal Treatment Profile has a secret unique identifier that can link the individual's Personal Profile (8). This allows the Natural and Artificial Intelligence (12) and business and social media networks to access this information without knowing the identity of the Person Being Treated.

11). Practitioner Treatment Criteria. Embodiments are designed to allow Subject Matter Experts, Doctors and Practitioners to define a wide range of Treatment Criteria. Each type of treatment and classification of Person Being Treated (1) along with the empirical results of their Personal Treatment Profile (10) is a factor in their treatment criteria. The Practitioner Treatment Criteria is used to guide the Natural and Artificial Intelligence (12). The Natural and Artificial Intelligence (12) may add its additional criteria for defining specific treatment protocol for each individual Person Being Treated (1).

12). Natural and Artificial Intelligence. Natural Intelligence [NI] possessed by humans can be captured and emulated by computing environments. In artificial intelligence, an expert system is a computer system that emulates the decision-making ability of a human expert. Expert systems are designed to solve complex problems by reasoning about knowledge, represented mainly as if—then rules rather than through conventional procedural code.

Complementing the NI component in the AINS system is an Artificial Intelligence [AI] component. NI captured in AI Expert systems may only address a subset of the computing required to deliver a real world solution. The additional component is Artificial Intelligence [AI]. AI addresses: Reasoning, Problem solving, Knowledge representation, Planning, Learning, Natural language processing, Perception, Motion and manipulation, Social intelligence, Creativity and General intelligence. Together these technologies properly informed, trained and directed allow the AINS to scale to massive numbers of concurrent users, on demand and in situation.

Figure 2:
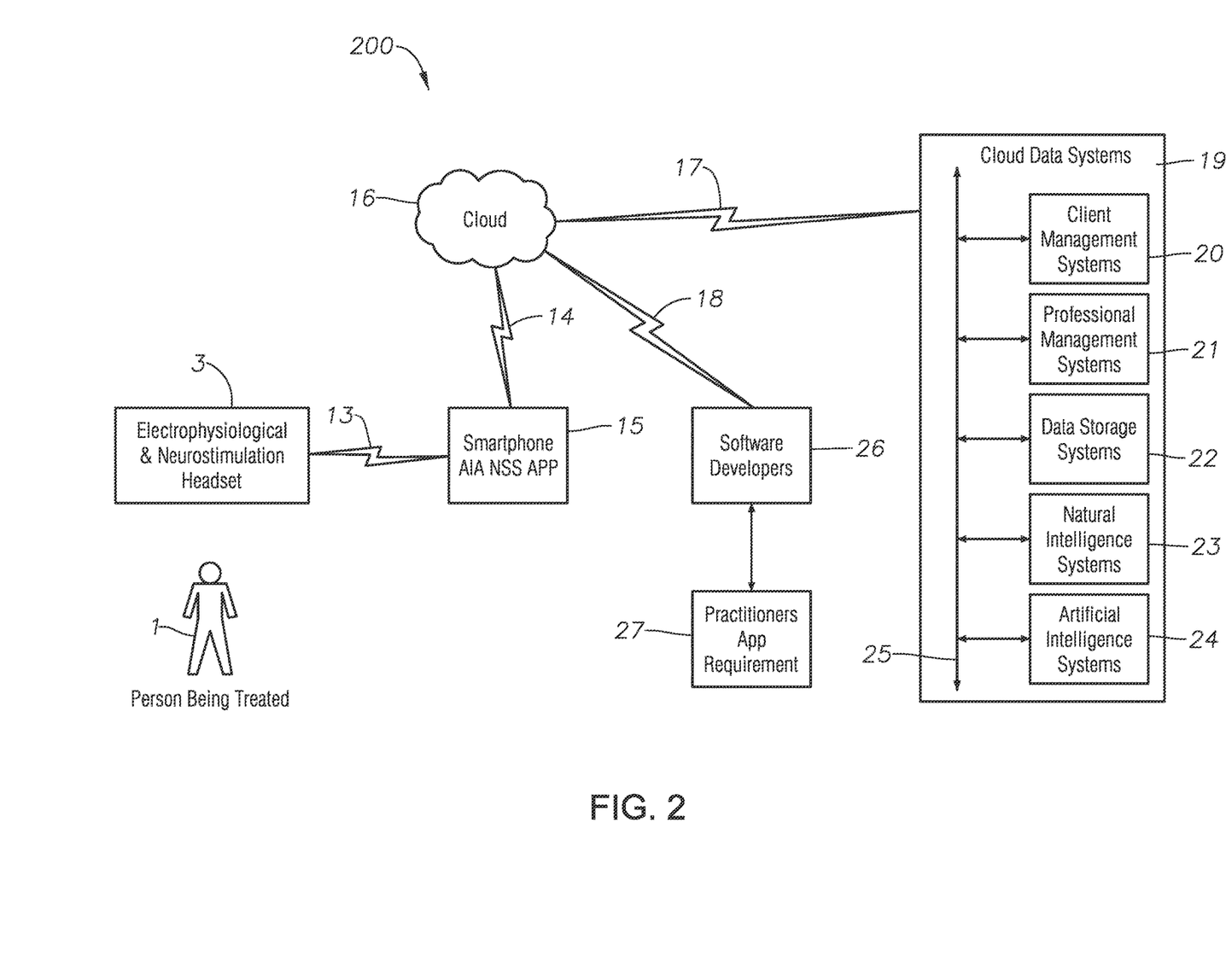
FIG. 2 is an AINS system diagram, according to an embodiment.

FIG. 2 is a diagram of an AINS system 200, according to an embodiment. Elements of the system 200 are described below, except where similar elements have been previously described with reference to FIG. 1.

13). First Remote Data Link. According to embodiments, an Electrophysiological & Neuro-stimulation Headset (3)

operatively communicates to Smartphone hardware and software networked computing platform (15) via a First Remote Data Link (13).

The preferred embodiment may employ Bluetooth. Bluetooth is a wireless technology standard for exchanging data over short distances (using short-wavelength Ultra High Frequency (UHF) radio waves in the Industrial, Scientific and Medical (ISM) band from 2.4 to 2.485 GHz) from fixed and mobile devices, and building Personal Area Networks (PAN).

Embodiments may employ Wi-Fi. Wi-Fi is a technology for wireless local area networking with devices based on the IEEE 802.11 standards. Wi-Fi most commonly uses the 2.4 Gigahertz (12 cm) Ultra High Frequency [UHF] and 5.8 Gigahertz (5 cm) Super High Frequency (SHF) Industrial, Scientific and Medical (ISM) radio bands.

The preferred embodiment may employ wireless Universal Serial Bus (USB). Wireless USB was based on the Ultra-Wide Band (UWB) common radio platform, which is capable of sending 480 Mbit/s at distances up to 3 meters (9.8 ft.) and 110 Mbit/s at up to 10 meters (33 ft.). UWB is designed to operate in the 3.1 to 10.6 GHz frequency range.

The preferred embodiment may employ Universal Serial Bus (USB). USB is an industry standard computer peripheral interface that defines cables, connectors and communications protocols for connection, communications, and electrical power between computers and external devices.

14). Second Remote Data Link. According to embodiments, a Smartphone hardware and software operatively couples to a networked computing platform 15 via a Second Remote Data Link (14) to the Internet. The Internet is the global system of interconnected computer networks that use the Internet protocol suite to link devices worldwide. It is a network of networks that consists of private, public, academic, business, and government networks of local to global scope, linked by a broad array of electronic, wireless, and optical networking technologies. The Internet carries a vast range of information resources and services, such as the inter-linked hypertext documents and applications of the World Wide Web, electronic mail, telephony, and file sharing.

The preferred embodiment may employ cellular telephone network connections. A cellular network or mobile network is a communication network where the last link is wireless. The network is distributed over land areas called cells, each served by at least one fixed-location transceiver, but more normally three cell sites or base transceiver stations. Cellular Mobile networks deliver voice and data over most of the inhabited land area of the Earth. This allows mobile phones and mobile computing devices to be connected to the Public Switched Telephone Network (PSTN) and public Internet.

The preferred embodiment may employ Wi-Fi. Wi-Fi is a technology for wireless local area networking with devices based on the IEEE 802.11 standards. Wi-Fi most commonly uses the 2.4 Gigahertz (12 cm) Ultra High Frequency (UHF) and 5.8 Gigahertz (5 cm) Super High Frequency [SHF] Industrial, Scientific and Medical (ISM) radio bands.

15). Smartphone. According to embodiments, a Smartphone hardware and software networked computing platform (15) delivers the User eXperience (UX) and provides the computing client and peripheral interface. The Smartphone computing platform (15) provides the hardware to connect to the Internet and interface with peripherals like the Electrophysiological & Neuro-stimulation Headset (3).

The smartphone (15) has the computing power to run a Mobile Operating System. A mobile Operating System (or mobile OS) is an operating system for phones, tablets and smartwatches or other mobile devices. Mobile operating systems combine features of a personal computer operating system with other features useful for mobile or handheld use. This includes: a touchscreen, cellular radio, Bluetooth radio, Wi-Fi Radio, Global Positioning System (GPS) mobile navigation Radio, still camera/video camera, speech recognition, voice recorder, music player, Near Field Communication (NFC), and infrared blaster.

The Smartphone computing platform (15) allows the development, installation and running of third party software applications know as APPS. Embodiments may provide a development community an application development framework and a suite of Application Programming Interfaces (APIs) that allow application specific treatments to be deployed in the AINS ecosystem. These applications allow specific focus on dysfunction, meditation and performance enhancement through access to the AINS Cloud Data Center (19) and its subsystems.

16). Cloud. Embodiments utilize an Internet accessed Computing Cloud (16) to interconnect the Smartphone computing client (15). Cloud computing metaphor: For a user, the network elements representing the provider-rendered services are invisible, as if obscured by a cloud. Cloud computing is a kind of Internet-based computing that provides shared processing resources and data to computers and other devices on demand.

17). Third Remote Data Link. Embodiments operatively couple the Internet Cloud 16 to the Internet connected Cloud Data Center (19). A Third Remote Data Link (17) to the Internet is provided by Internet Service Providers. This Internet connection uses the Public Switched Telephone Network (PSTN) to transport Internet Protocol (IP) data to and from the AINS Smartphone (15) and the AINS provisioned Cloud Data Center (19).

19). Cloud Data Center. Embodiments utilize an Internet accessed Cloud Data Center (19) to manage the plurality of services that must be deployed to deliver the AINS services and treatments. A data center is a facility used to house computer and data storage systems along with the required services: Uninterruptable Power Supplies (UPS), Uninterruptable Telecommunications, Uninterruptable Cooling, Fire Suppression, Data and Physical Security.

The Cloud Data Center (19) may be a private facility purpose built to deploy AINS, or it may be delivered as a Cloud Data Center service that allows rack space, bare iron or fully provisioned servers. The Cloud Data Center (19) may provide the computing and networking infrastructure to house and deliver the multiplicity of computing services an AINS service requires.

All services in the AINS Cloud Data Center (19) may be auto scaling and load balanced to allow uninterrupted dynamic expansion of services required to service millions to tens of millions of concurrent users.

20). Client Management Systems. Client Management Systems (20) is a multiplicity of computing systems required to deliver a secure set of services that may manage all the users of the AINS system. Each user including: managers, owners, operators, end users, developers, may have accounts allowing them access to the systems and services contained in the AINS Cloud Data Center (19).

21). Professional Management Systems. Professional Management Systems (21) may deliver the services required by the professional users of AINS embodiments. This class of users may require additional services beyond the offering of the Client Management Systems (20). Additional data security, privacy and branding may be delivered through the Professional Management Systems (21).

22). Data Storage Systems. A multiplicity of Data Storage Systems (22) may be utilized in the AINS Cloud Data Center (19). All data generated from Research and Development, Service Development, Hardware and Software development, Professional Expertise, Expert Training of Natural and Artificial Intelligence (12), User Personal Profiles (8), User Personal Treatment Profiles (10), Natural Intelligence Systems (23) Artificial Intelligence Systems (24).

23). Natural Intelligence Systems. The Natural Intelligence Systems (23) may be configured with the proper compute, storage and networking capacity required to run the selected software. Natural Intelligence Systems (23) may be provisioned and deployed at the AINS Cloud Data Center (19) to capture and deliver subject matter expert natural intelligence instantiated into the expert systems that make up the Natural Intelligence Systems (23).

24). Artificial Intelligence Systems. Artificial Intelligence Systems (24) may be configured with the proper compute, storage and networking capacity required to run the selected software. Artificial Intelligence Systems (24) may be provisioned and deployed at the AINS Cloud Data Center (19) to capture and deliver subject matter expert training required to allow Machine Intelligence beyond the Natural Intelligence Systems (23).

25). Networking & Software Bus. Computer Networking & Software Buses (25) may be utilized to interconnect all of the systems operating in the AOA NSS Cloud Data Center (19). A multiplicity of networking technologies and protocols may be selected to deliver the required the performance, availability and security.

A software bus is a software architecture model where shared communications channels facilitate connections and communications between software modules. This makes software buses conceptually similar to the bus term used in computer hardware for interconnect.

26). Software Developers. The AINS system and related services require multiple levels of software development. Software Developers (26) may architect the framework and write the computer codes to create and maintain all of the systems required to deliver the AINS systems and services. This includes:

Electrophysiological & Neuro-stimulation Headset (3)
Smartphone AINS APPs (15)
Client Management Systems (20)
Professional Management Systems (21)
Data Storage Systems (22)
Natural Intelligence Systems (23)
Artificial Intelligence Systems (24)

27). Practitioner App Requirement. The AINS system and related services require practitioner and related subject matter experts to define the process, procedures and protocols so the Software Developers (26) can architect the framework and write the computer codes to create and maintain all of the systems required to deliver the AINS systems and services.

Figure 3:
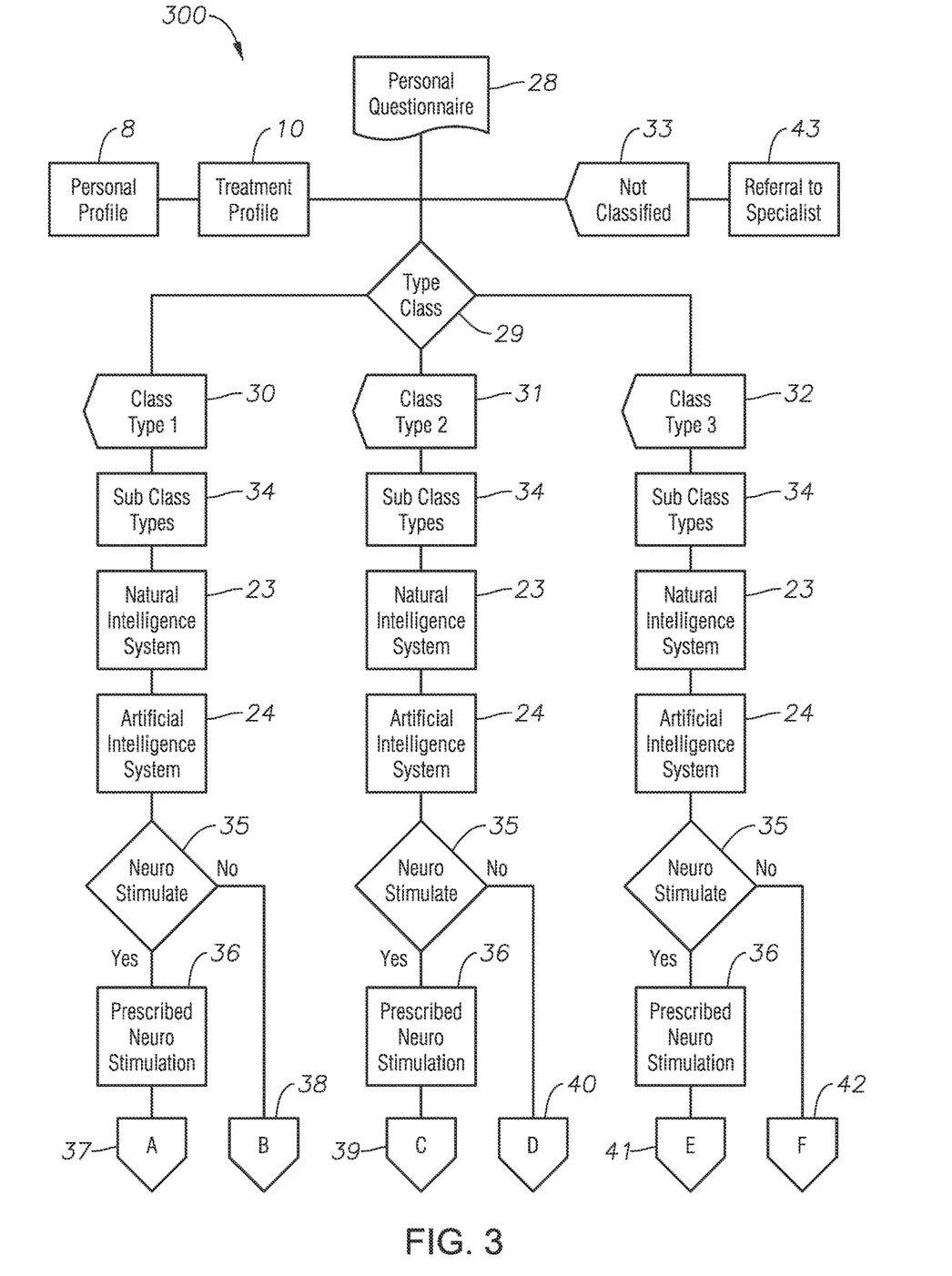
FIG. 3 is a first portion of an AINS flow chart, according to an embodiment.

FIG. 3 is a first portion 300 of an AINS flow chart, according to an embodiment, including the elements described below:

8). Personal Profile, as described above with reference to FIG. 1. 10).

Personal Treatment Profile, as described above with reference to FIG. 1.

28). Personal Questionnaire. Personal Questionnaire (28) is an online form that starts the assessment process for the Person Being Treated (1) to create an account. The questionnaire is one modality to collect relevant information required to create an account, define payments, and assess sensitivity, preferences, pre-existing conditions and related information.

29). Type Classification. Once the Person Being Treated (1) has successfully created an account the Natural and Artificial Intelligence (12) may classify and weigh the individual along a range of abstract classification categories that are defined by the practitioner, Doctors and subject matter experts. These type classifications (29) may directly influence the Neurofeedback & Neuro-stimulation types, intensity, location, frequency and dosage as prescribed by the Natural and Artificial Intelligence (12) and respective systems (23) (24).

30). Type 1 Classification. The Type 1 classification (30) may be a designation defined by the Person Being Treated's (1) sensitivity to neurofeedback, neuro-stimulation, light, sound, smell, touch, and related parameters that the Natural and Artificial Intelligence (12) has been instructed to evaluate and classify.

31). Type 2 Classification. The Type 2 classification (31) may be a designation defined by the Person Being Treated's (1) ability and capacity to respond to neurofeedback, neuro-stimulation, light, sound, smell, touch, and related parameters that the Natural and Artificial Intelligence (12) has been instructed to evaluate and classify.

32). Type 3 Classification. The Type 3 classification (32) may be a designation defined by the Person Being Treated's (1) ability to resist neurofeedback, neuro-stimulation, light, sound, smell, touch, and related parameters that the Natural and Artificial Intelligence (12) has been instructed to evaluate and classify.

33). Not Classed. Not Classed (33) is a designation defined for the Person Being Treated (1) who has not successfully completed the account creation process or has not delivered reliable or consistent information, or is not suitable for AINS Neurofeedback/Neuro-stimulation treatment.

34). Sub Class Types. Sub classification types (34) may be added to the weighted ranges defined in the classifications (30) (31) (32). The Person Being Treated (1) may need to further define parameters and values that the Natural Intelligence (23) and the Artificial Intelligence Systems (24) use to further refine the assessment, prescriptions and treatments. These sub class types may include: irritability, head trauma history, anxiety activation, symptoms, energy regulation, cognitive and emotional difficulties, pain, movement difficulties, medications, medical diagnosis & health.

23). Natural Intelligence Systems. (As described above with reference to FIG. 2.)

The Natural Intelligence Systems (23) may perform the first level of assessment in determining the set of parameters and values it may communicate to the Artificial Intelligence Systems (24) for each individual Person Being Treated (1).

24). Artificial Intelligence Systems. (As described above with reference to FIG. 2.)

Once the Natural Intelligence Systems (23) has completed its assessment the Artificial Intelligence Systems (24) may take what it has learned from its original training and combine that with what the Natural Intelligence Systems (23) has communicated and combine that with what it has learned from doing a multiplicity of treatments on a multiplicity of Persons Being Treated (1).

35). Neuro Stimulate. Once all the assessment and analysis is complete, the treatment session running on the Person Being Treated's (1) Smartphone (15) that is communicating with the Electrophysiological & Neuro-stimulation Headset (3) and the AINS Cloud Data Center (19) may render a command to neuro stimulate at the defined parameters and values. Or the Natural Artificial Intelligence (12) may prohibit the neuro-stimulation to take place.

36). Prescribed Neuro-stimulation. If the Neuro Stimulate (35) is YES then the Natural Artificial Intelligence (12) prescribed neuro-stimulation may be administered to the Person Being Treated (1).

37). Flowchart A Path Continuation to FIG. 4 (FIG. 4)
38). Flowchart B Path Continuation to FIG. 4 (FIG. 4)
39). Flowchart C Path Continuation to FIG. 4 (FIG. 4)
40). Flowchart D Path Continuation to FIG. 4 (FIG. 4)
41). Flowchart E Path Continuation to FIG. 4 (FIG. 4)
42). Flowchart F Path Continuation to FIG. 4 (FIG. 4)

43). Refer to Specialist. In the event that the AINS Natural Artificial Intelligence (12) virtual practitioner has enough valid information and believes that the Person Being Treated (1) may be better served by a referral to a real specialist that is an actual person qualified to treat, then the referral may be made.

Figure 4:
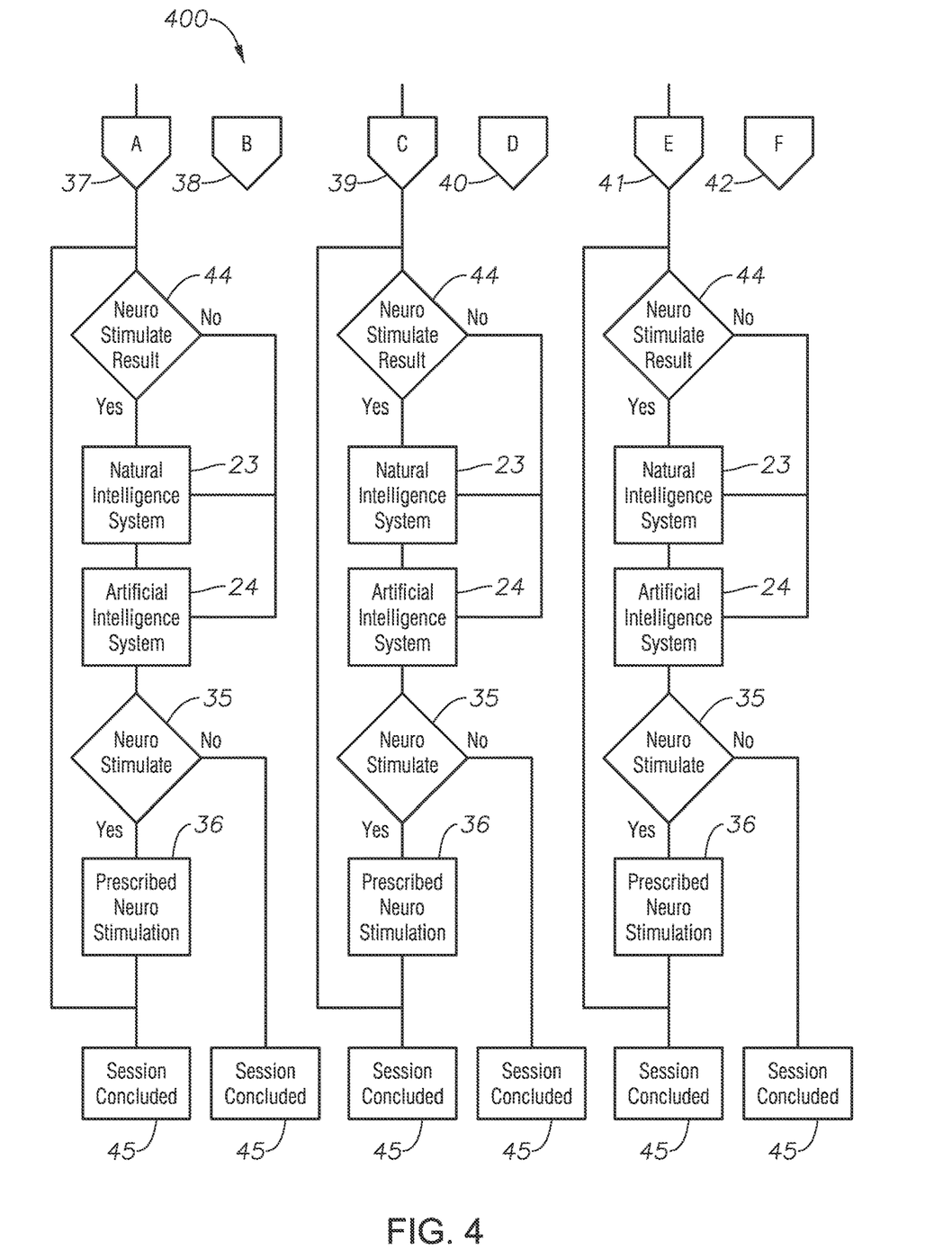
FIG. 4 is a second portion of the AINS flow chart of FIG. 3, according to an embodiment.

FIG. 4 is a second portion 400 of the AINS flow chart of FIG. 3, according to an embodiment, as described below:

37). Flowchart A Path Continuation from FIG. 3 (FIG. 3) to FIG. 4 (FIG. 4)
38). Flowchart B Path Continuation from FIG. 3 (FIG. 3) to FIG. 4 (FIG. 4)
39). Flowchart C Path Continuation from FIG. 3 (FIG. 3) to FIG. 4 (FIG. 4)
40). Flowchart D Path Continuation from FIG. 3 (FIG. 3) to FIG. 4 (FIG. 4)
41). Flowchart E Path Continuation from FIG. 3 (FIG. 3) to FIG. 4 (FIG. 4)
42). Flowchart F Path Continuation from FIG. 3 (FIG. 3) to FIG. 4 (FIG. 4)

44). Neuro Stimulate Result. Once the Prescribed Neuro-stimulation (36) has been administered the Natural Artificial Intelligence (12) may make an assessment if the neuro-stimulation was successful. This affirmation may also include a query with the Person Being Treated (1) to have them describe any changes that they may be aware of.

The Natural Intelligence Systems (23) and the Artificial Intelligence Systems (24) may analyze all relevant information and determine the next steps in the procedure. Multiple successive neuro-stimulations (35) may be administered after a waiting period between each. Other results may require modifications to the parameters and values of the prescribed neuro-stimulation. Yet others may not require further treatment.

35). Neuro Stimulate. Once all the assessment and analysis is complete, the treatment session running on the Person Being Treated's (1) Smartphone (15) that is communicating with the Electrophysiological & Neuro-stimulation Headset (3) and the AINS Cloud Data Center (19) may render a command to repeat the neuro stimulate at the defined parameters and values. Or the Natural Artificial Intelligence (12) may prohibit the neuro-stimulation to take place.

36). Prescribed Neuro-stimulation. If the Neuro Stimulate (35) is YES then the Natural Artificial Intelligence (12) prescribed repeat neuro-stimulation may be administered to the Person Being Treated (1). This process of Neuro Stimulate Decision (35) followed by the Prescribed Neuro-stimulation (36) followed by the Neuro Stimulate Result Decision (44) as communicated by the Person Being Treated (1) confirmed by the assessment of the Natural Intelligence Systems (23) and the Artificial Intelligence Systems (24) can be repeated as many times as required.

45). Session Concluded. If the Neuro Stimulate (35) is NO, then the Natural Artificial Intelligence (12) has determined that no further iterations of prescribed neuro-stimulation are required, and the session may be concluded.

Artificial Intelligence Neural Stimulation System [AINS] embodiments include a Client Server computing Model that integrates the following systems and sub systems:
End User Client System:
IR LED Emitter (2)
Electrophysiological & Neuro-stimulation Headset (3)
Smartphone (15)
AINS Treatment Specific Software Applications
Smartphone Remote Connection (13) to Electrophysiological &
Neuro-stimulation Headset (3)
Smartphone Remote Connection (14) to Internet Cloud (16)
Cloud Connection (17) to Cloud Data Center (19)
Internet Based Cloud Computing System:
Cloud Data Center (19) Configured for AINS
Client Management Systems (20)
Professional Management Systems (21)
Data Storage Systems (22)
Natural Intelligence Systems (23)
Artificial Intelligence Systems (24)
Data Center Networking and Software Bus (25)
User Social Communities
Developer Social Communities
Professional Social Communities Together these systems are designed to augment and in many cases replace the practitioner that may typically treat a person with neuro-stimulation. Having practiced neuro-stimulation for over a decade on 100s of individuals it was revealed that this process could be augmented with Artificial intelligence systems. Furthermore it was evident that most individuals required daily or weekly neuro-stimulation to obtain the desired results. This is logistically problematic due to repeated scheduling, travel and expenditure.

Analysis of the assessments, prescriptions and treatments of neuro-stimulation individuals may contribute to development of the AINS system. The first step undertaken, according to embodiments, is the creation of a non-obtrusive wireless and wired Electrophysiological & Neuro-stimulation Headset (3).

According to an embodiment an inexpensive Headset (3) (that an individual may own) may enable, with the consultation of a virtual practitioner enabled by the Natural & Artificial Intelligence (12), self-treatment at substantially any location on demand as needed.

AINS embodiments include the ability to connect the Electrophysiological & Neuro-stimulation Headset (3) to a Smartphone (15) that can run a multiplicity of treatment specific applications (APPS). The APPS are developed by a collaboration of Practitioners I Subject Matter Experts (27) and Software Developers (26).

Together the subject matter experts and the engineering development teams define the End User Client Systems and the Internet Based Cloud Computing System. Once these systems are created additional work needs to be performed by the subject matter experts. The Natural Intelligence Systems (23) need to be loaded with the Expert Systems information related to each use case.

A Person wishing to become a Person Being Treated (1) may be directed to the AINS service branded website or be linked from the AINS APP downloaded and installed on their Smartphone (15). This may begin the registration process which may collect relevant information required to create an account. The same process may be used for developers and professionals however they may each have a unique web portal URL [Uniform Resource Locator] that directs them to the appropriate community.

Once the individual has created an account they may be directed to the Personal Questionnaire (28) that may be delivered as a web-centric interactive session to determine the sensitivity, seizure propensity, anxiety levels and related health issues. Once the AINS has determined that the registered individual is an appropriate candidate for becoming a Person Being Treated (1) then they may be directed to the URL that allows them to obtain the Electrophysiological & Neuro-stimulation Headset (3). If the AINS determines that the individual trying to register for an account is not classified (33) or appropriate, they may be denied an account or referred to a live practitioner (43).

Once the individual has received their Electrophysiological & Neuro-stimulation Headset (3) they may be required to run the AINS APP on their Smartphone (15) and follow the procedure to properly connect their Electrophysiological & Neuro-stimulation Headset (3) so they can take the next steps to establish their Electrophysiological baseline.

The Person Being Treated (1) may run an AINS APP on their Smartphone (15) that is paired to their Electrophysiological & Neuro-stimulation Headset (3). This End User computing environment may establish a connection to the Cloud Data Center (19) and store all relevant information in their Personal Profile (8) that is managed by the Client Management Systems (20). The Client Management Systems (20) may initiate a session for the Person Being Treated (1) which may allocate resources from the Data Storage Systems (22), the Natural Intelligence Systems (23) and the Artificial Intelligence Systems (24).

The AINS App running on the Person Being Treated's (1) Smartphone (15) may guide them through the process of getting the Electrophysiological & Neuro-stimulation Headset (3) to begin sending electrophysiological and Magnetoencephalography [MEG] and or EEG brainwaves to the Smartphone (15) app. During this process if at any time the hardware, software or user are not performing correctly the Natural Intelligence Systems (23) and the Artificial Intelligence Systems (24) may assess and guide the user through the process, while automatically performing any firmware or software updates required to provision the Electrophysiological & Neuro-stimulation Headset (3) and associated Smartphone (15).

Once the Person Being Treated's (1) Smartphone (15) and Electrophysiological & Neuro-stimulation Headset (3) is sending data to the Cloud Data Center (19) session a series of activities may be communicated in order to establish a baseline. After the baseline is successfully created and stored in the Personal Profile (8) the Person Being Treated (1) may be instructed how-to get ready to execute the procedure defined in the flowchart (FIG. 3, FIG. 4).

The Person Being Treated (1) may choose a dysfunction, meditation or performance enhancement treatment protocol they wish to engage in by downloading and running the corresponding software application (APP) on to their Smartphone (15). The APP may connect to the Cloud Data Center (19) and register the Person Being Treated (1) through a Login and authentication process. Once the Login is successful the Person Being Treated (1) may initiate a session that may be managed by the Client Management Systems (20).

The Client Management Systems may manage the session by allocating services from the Storage Management System (22), the Natural Intelligence System (23) and the Artificial Intelligence Systems (24) that may deliver specific actions for the Person Being Treated (1) to take. These can be presented as a virtual Doctor, Practitioner, Subject Matter Expert or similar virtual human.

First the Natural Intelligence Systems (23) may perform all of the deductive logical processes required to prepare the session and the Person Being Treated (1) for their treatment.

The Natural Intelligence Systems (23) includes:
1. Natural Language Lexicon
2. Controlled Vocabulary
3. Ontology
4. Fact-List
5. Instance-List
6. Knowledge Base
7. Rule-Base
8. Inference Engine The Natural Intelligence Systems (23) capture the stored knowledge of the collective group of the Subject Matter Experts and serves a fact checking and query information repository for the class of problems that can be addressed with if-then logic. Formal Theory and Material Conditional Theory imply a Logical Connective: if P then Q. The antecedent P is the first half of a hypothetical proposition, whenever the if-clause precedes the then-clause. The Q consequent is the second half of a hypothetical proposition. Together large collections of if—then statements can traverse the NI knowledge base and define the assessment, treatment history and other non-cognitive learning functions.

Once the Natural Intelligence Systems have satisfied their criteria for proceeding, the data set may be transferred to the Artificial Intelligence Systems (24) for Inductive activities related to the session. The Artificial Intelligence Systems (24) have access and understanding of every Person Being Treated (1) and every treatment protocol and session ever conducted in the AINS. This knowledgebase provides an unprecedented level of knowledge.

The Artificial Intelligence Systems (24) perform the cognitive learning functions as Machine Intelligence. The Artificial Intelligence Systems (24) include the following:
1. Artificial Neural Networks
2. Association Rule Learning
3. Bayesian Networks
4. Clustering
5. Decision Tree Learning
6. Deep Learning
7. Genetic Algorithms
8. Inductive Logic Programming
9. Learning Classifier Systems
10. Markov networks
11. Probabilistic Graphical Models
12. Reinforcement Learning
13. Representation Learning
14. Rule-based Machine Learning
15. Similarity and Metric Learning
16. Sparse Dictionary Learning The AI systems may have the ability to use multiple types of data including multiple media types: temporal data, images, video, sounds, graphs, physiological data, medical data, diagnostic imaging, brain waves, text, databases, markup languages, ontologies, annotations, tagging and other related data types as required to deliver AINS services and service improvements.

Together the practitioner driven Natural Intelligence Systems (23) augmented by the Artificial Intelligence Systems (24) creates a feedback loop from the responses given and measured from the Person Being Treated (1). The neuro-stimulation may be administered in an Open Loop or a Closed Loop protocol depending on certain conditions. Traditionally Open Loop was performed due to a lack of feedback technologies. The AINS provides an Electrophysiological & Neuro-stimulation Headset (3) that incorporates a multiplicity of sensors that can provide additional feedback beyond what the Person Being Treated (1) reports directly.

By closing the loop on the treatment protocols, the Natural Intelligence Systems (23), the Artificial Intelligence Systems (24) and the subject matter experts can learn from the experiences of each individual Person Being Treated (1) additionally, the ability to suggest sophisticated combinations of Neuro-stimulation can be explored and integrated into everyday treatment options.

Figure 5:
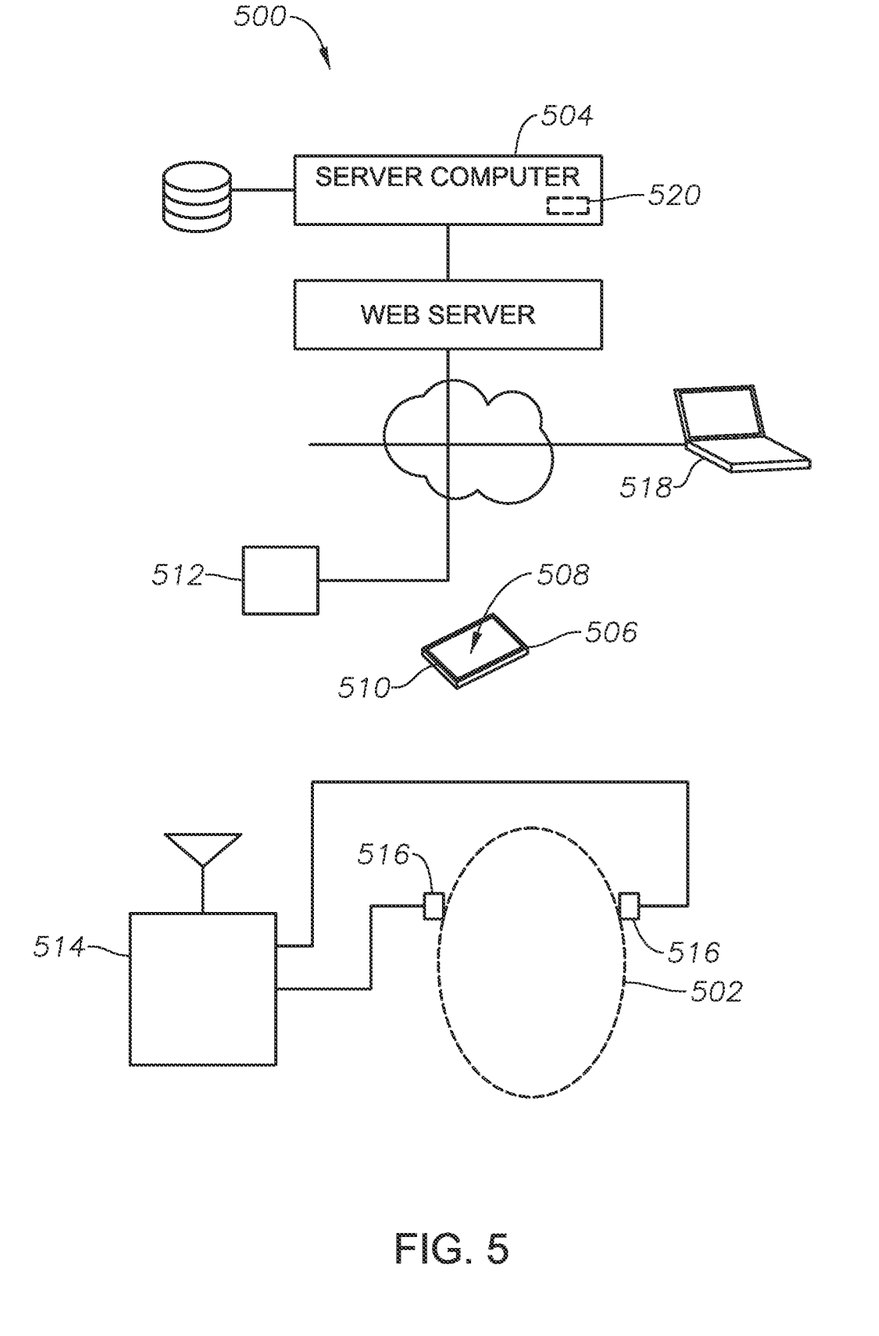
FIG. 5 is a diagram of a system for providing a low energy therapeutic field to the head of a user, according to an embodiment.

FIG. 5 is a diagram of a system 500 for applying a low energy neuro-stimulation therapeutic field to one or more locations adjacent to a user's head 502, according to an embodiment. The system may generally be driven by a computer program downloaded from a server computer 504 into a local computing device 506 such as a cell phone or the like.

The local computing device 506 may be operated by the user 502 via a graphical user interface (GUI) 508 displayed on an electronic display 510. Additionally or alternatively, the local computing device 506 may include a program operated remotely by a neuro-stimulation practitioner via a graphical user interface on a practitioner device 518. Additionally or alternatively, a treatment program in the local computing device 506 may operate responsive to input from both the user 502 via the GUI 508 on the electronic display 510 and from the remote practitioner via the practitioner device 518.

According to embodiments, the downloaded program may output sensed information to the practitioner device 518 such that the practitioner may monitor the condition of the user. For example, the downloaded program may stream video or send periodic photos of the user captured by a camera module 512 included in the local computing device 506. According to an embodiment, the practitioner device 518 displays a STOP control to the practitioner while the practitioner monitors a treatment. In case of an unintended response of the user witnessed by the practitioner, the practitioner may cause a treatment field to be removed by actuating the STOP control.

The local computing device 506 may include a camera platform 512 and a sensor platform operatively coupled to a computer circuit including a logic device (such as a microprocessor, processing core(s) or programmable logic device) and computer readable non-transitory memory capable of holding the computer application program for execution by the logic device. The local computing device includes a radio platform capable of outputting a radio signal operatively coupled to communicate with wireless network radio, optionally one or more Bluetooth coupled devices (not shown) disposed adjacent to the user's cranium 502, and optionally a low energy field treatment apparatus 514 such as a LENSWARE 3 system, available from Ochs Labs, Sebastopol, California.

The local computing device 506 receives a signal from the one or more devices or the treatment apparatus 514 corresponding to a user 502 brainwave.

Generally speaking, the apparatus 514 or the computer program interacts with other portions of the system 500 to detect an electric field signal from one or more predetermined extracranial positions adjacent the user's head 502 and detect a principal frequency in the electric field signal, the electric field signal and the principal frequency being referred to as a brainwave. The program or the apparatus 514 generates a treatment signal that is a function of the brainwave. Notably, the program or the apparatus 514 generates a treatment signal that is about 5 to 20 Hz different than the detected principal frequency and causes the treatment signal to generate a treatment field at or near the predetermined extracranial positions. The computer program may prompt the user to place electrodes 516 or devices according to a schedule of predetermined locations and/or parameter.

In an embodiment of a measurement mode, the computer program detects brainwaves at each of a plurality of guided extracranial positions and determines a treatment position based on brainwave characteristics. For example, the computer program may detect a position corresponding to a highest amplitude signal and guide the user to place the electrodes or devices near the highest amplitude signal.

In another embodiment of a measurement mode, the electrodes 516 or devices may include an array of electrodes or devices. In the case of an electrode or device array, the electrodes or devices may be held at a plurality of relatively fixed extracranial positions, and the computer program may cause the local computing device 506 or the apparatus 514 to poll the positions to determine treatment positions.

In a treatment mode, the computer program 521 causes the system 500 to apply the treatment signal in a series of envelopes. In an embodiment, the system 500 reenters the measurement mode between treatment signal envelopes.

The inventor contemplates various types of treatment fields. In one embodiment, the treatment field includes a low amplitude electrostatic field applied through the electrodes 516 and/or audio devices. In another embodiment, the treatment field includes a sub-audible auditory or pulsed light signal respectively generated by audio devices, electronic display 510, or illuminator controlled by the camera module 512. In another embodiment, the sensor platform, audio devices or apparatus 514 may include a magnetic field generator, an ultrasound generator, or an illuminator such as an infrared or red light emitter to respectively produce a treatment field.

In an embodiment, the system 500 may include operative coupling to a practitioner device 518. From the practitioner device 518, the practitioner may view treatment results, parameter(s), schedule(s), and user feedback. The practitioner may enter a message to the user and/or update the parameter(s) and/or schedule(s) based on expert knowledge. In an embodiment, the server computer supports an artificial intelligence (AI) program 520 configured to compare user treatment result(s), parameter(s), schedules(s), and user feedback to the practitioner message to the user and/or update the parameter(s) and/or schedule(s), and apply a plurality of so witnessed monitoring and diagnostic sessions to develop artificial expert knowledge to control the neuro-stimulation. In an embodiment, the AI 520 prompts the practitioner via the practitioner device 518 according to its artificial expert knowledge. The AI 520 thus refines its model.

Figure 6:
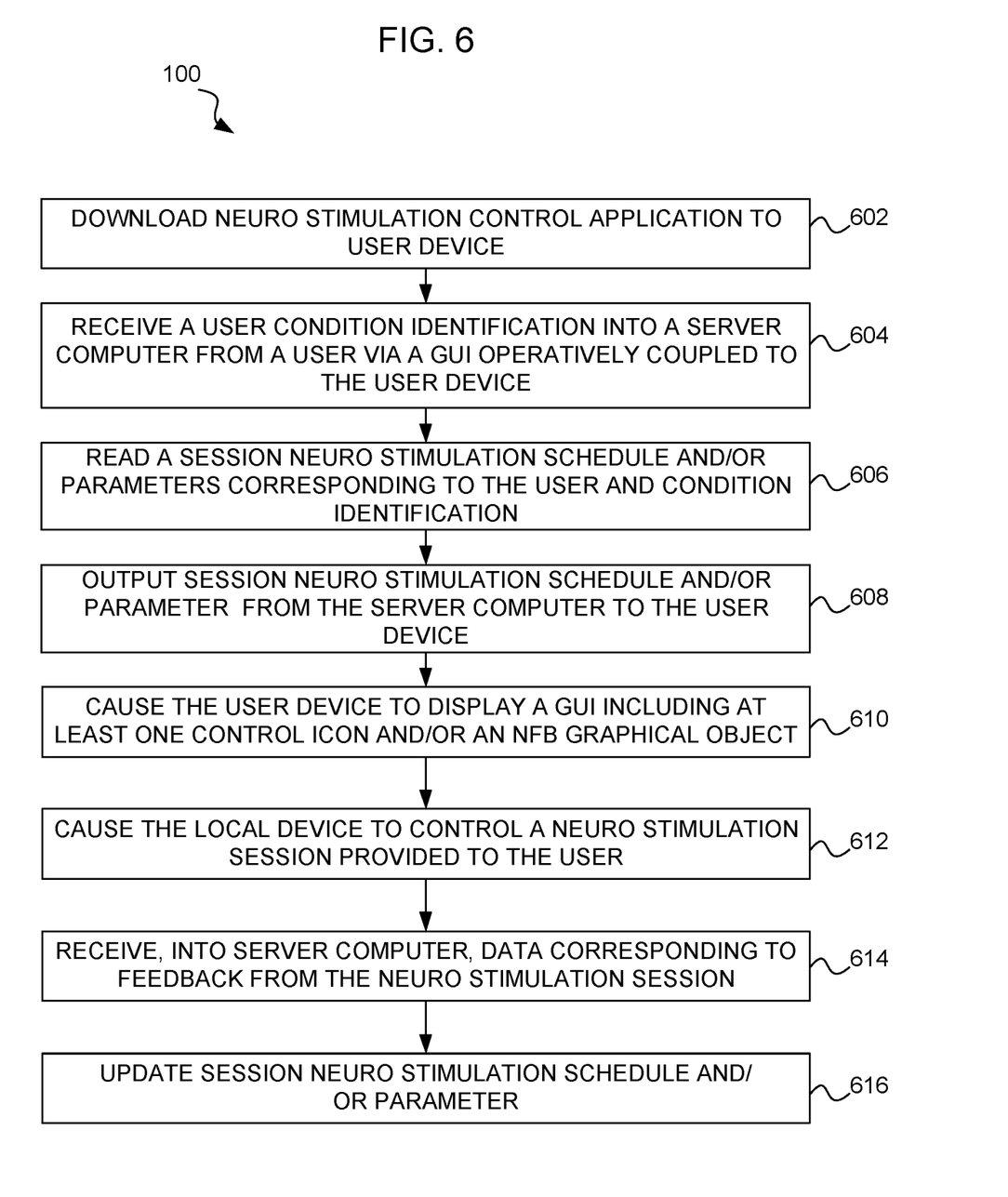
FIG. 6 is a flow chart showing a method for applying neuro-stimulation, according to an embodiment.

FIG. 6 is a flow chart showing a method 600 for applying neuro-stimulation, according to an embodiment. According to an embodiment, a method 600 for applying neuro-stimulation includes, in step 604, receiving, into a server computer via a graphical user interface of a user device, a condition identification corresponding to a condition experienced by a patient, wherein the condition is treatable by neuro-stimulation. Step 606 may include reading, from a non-transitory computer-readable medium, a session neuro-stimulation schedule corresponding to the condition from a plurality of neuro-stimulation schedules corresponding to respective conditions, and, in step 608, outputting the session stimulation schedule and/or parameter from the server computer to the user device. In an embodiment, step 610 includes causing the user device to display a control graphical user interface. The method may include enabling the user device to control a neuro-stimulation headset for applying the session neuro-stimulation schedule.

The method 600 may further include causing the user device to display a control graphical user interface, and receiving user input via the control graphical user interface to start a neuro-stimulation session using the neuro-stimulation schedule, whereupon the neuro-stimulation session is started.

According to an embodiment, the method may include causing the user device to display a control graphical user interface and receiving user input via the control graphical user interface to stop or pause a neuro-stimulation session, whereupon a current neuro-stimulation session is paused or halted.

In an embodiment the session neuro-stimulation schedule and/or parameter includes feedback setpoints for receiving feedback from at least one of the user, via a graphical user interface, and a sensor disposed in the neuro-stimulation headset. Enabling the user device to control the neuro-stimulation headset may include enabling the user device to control neuro-stimulation output according to feedback included in the neuro-stimulation schedule.

Enabling the user device to control a neuro-stimulation headset for applying the session neuro-stimulation schedule may include controlling the neuro-stimulation headset for applying the session neuro-stimulation schedule to a user. Controlling the neuro-stimulation headset may include causing the neuro-stimulation headset to output an electrostatic field to the user. Causing the neuro-stimulation headset to output the electrostatic field to the user may include applying a periodic field characterized by an oscillation frequency derived from and not equal to a detected principal frequency of a brainwave.

According to embodiments, applying a periodic field characterized by an oscillation frequency derived from and not equal to a detected principal frequency of a brainwave may include applying a periodic field one to one-hundred hertz greater than or less than the detected principal frequency of the brainwave. According to an embodiment, applying a periodic field different than the detected principal frequency includes selecting an offset as a function of a sensitivity of the person undergoing the treatment. For example, one person may respond best to an applied frequency five Hertz greater than or less than the principal frequency, and another person may respond best to an applied frequency twenty Hertz or more (up to about 100 Hz) greater than or less than the detected principal frequency of the brainwave.

According to embodiments, the neuro-stimulation headset includes two emission devices positioned proximate respective selected positions on the user's cranium.

In an embodiment, controlling the neuro-stimulation headset includes causing the neuro-stimulation headset to output a magnetic field to the user. In another embodiment, controlling the neuro-stimulation headset includes causing the neuro-stimulation headset to output a sonic field to the user. In another embodiment, controlling the neuro-stimulation headset includes causing the neuro-stimulation headset to output a trans-epidural light field to the user.

Various positive responses to neuro-stimulation are contemplated by the inventor. For example, controlling the neuro-stimulation headset for applying the session neuro-stimulation schedule to a user may cause disentrainment of user habitual thought patterns. "Disentrainment" refers to the disruption of habitual thought patterns (conscious and/or subconscious) via the application of appropriate neural stimulation. Since such habitual thought patterns may be regarded as running in "a loop" that correlates to a brain-wave frequency, the application of an off-frequency treatment field causes an impetus to "reset" such loops to reduce undesirable thought patterns, in other words, to cause "disentrainment".

Causing the user device to display a control graphical user interface in step 610 may include causing display of at least a "start session" graphical control object. Additionally or alternatively, causing the user device to display a control graphical user interface includes causing display of one or more objects for user response during neuro-stimulation. The one or more objects provide at least a portion of the feedback.

In step 612, which may be indirectly executed via the downloaded application, the server computer causes the user electronic device to control a neuro-stimulation session provided to the user.

The method may further include step 614, including receiving data corresponding feedback from the session neuro-stimulation session and, in step 616, updating the session neuro-stimulation schedule and/or parameter by writing, to the non-transitory computer-readable medium, the received data. In an embodiment, writing the received data to the non-transitory computer-readable medium causes the session neuro-stimulation schedule corresponding to the condition to be modified according to received data.

Feedback used in the method may include biofeedback.

Figure 7:
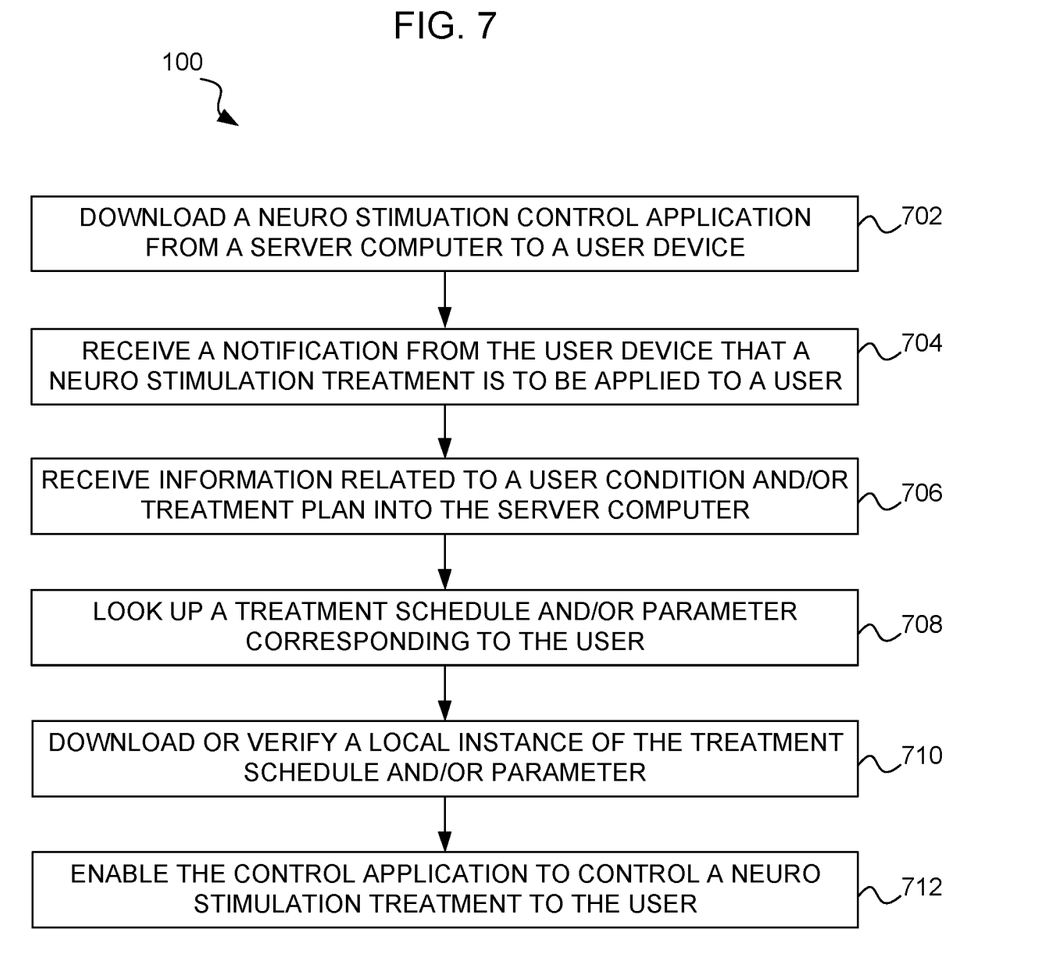
FIG. 7 is a flow chart showing a method for applying a neuro-stimulation therapeutic field to a user, according to another embodiment.

FIG. 7 is a flowchart showing a computer method 700 for operating a server computer to provide a cranial nerve tissue stimulation system, according to embodiments. Step 704 includes receiving, into a server computer, a notification from a user computing device that a low energy treatment to be applied to a human user's cranium is to be performed. Optionally, the method 700 may include reading a UUID or account profile from the user computing device as a verification of a user identity. Optionally, the method 700 may include receiving, such as from a secure enclave in a user device, a response to a digital challenge. The response to the digital challenge may be provided, in part, by a user biometric response.

Proceeding to step 706, information related to a user condition is received into the server computer. For example, the user condition may be included in an account profile, and the step of receiving the information related to the user condition may include reading the user condition from the account profile. For example, the account profile may include a diagnosis made by a physician or other licensed practitioner for at-home use by the user. Additionally or alternatively, the information related to the user condition may be obtained according to a user entry.

Step 708 includes looking up a treatment schedule corresponding to the user condition, followed in step 710, by downloading to or verifying a local instance of the treatment schedule, the local instance including data disposed on a computer readable non-transitory medium, the data being arranged to cause a local application to cause a very low energy treatment to be applied to the human user's cranium. In an embodiment, responsive to locally generated parameters, the treatment schedule causes an emission of low energy therapeutic field coupled to a human cranial nerve, the low energy therapeutic field being selected responsive to at least one detected or inferred human user condition. In an embodiment, a characteristic of the applied low energy therapeutic field is determined according to remote local processing by the user computing device.

As an alternative to downloading or verifying a local instance, the inventor contemplates providing a web application interface configured to cause the the user computing device to control application of the therapeutic field according to the treatment schedule.

In an embodiment, the treatment schedule is selected responsive to at least one contemporaneous user input or response. The treatment schedule may be responsive to sensed data. The sensed data may be obtained by a user computing device sensor platform. In an embodiment, the sensed data is obtained by an explicit user response to a prompt on a GUI displayed on an electronic display. In an embodiment, the sensed data is obtained by a camera module. For example, the application may cause the user computing device to receive camera module frames including an area of the user's skin. The application may compare a frame to one or more previous frames and determine whether a blood flush to the skin during a treatment indicates the treatment at the location shall stop.

In an embodiment, the sensed data includes vocal utterances of the user. In an embodiment, the sensed data includes a detected brainwave.

The method 700 may further include, in step 702, downloading a computer application configured to run on the user computing device to obtain sensor data contemporaneously with the treatment, compare the contemporaneous sensor data to the treatment schedule, and cause hardware to output the therapeutic field to be received by the human cranial nerve.

Various therapeutic fields are contemplated. In an embodiment, the low energy therapeutic field includes a low energy electrostatic field. The low energy electrostatic field may be electro-capacitively coupled to a region of the human cranium corresponding to a location where the brainwave is detected. In an embodiment, the low energy electrostatic field is operatively coupled to an emission device proximate to the human cranium.

Various approaches may be used to generate a therapeutic field of an appropriate field strength. For example, a low energy electrostatic field may be driven by a logic level drive voltage. In another example, a low energy electrostatic field may be driven from a logic level drive voltage through an amplifier having a gain less than 1.

In an embodiment, a low energy electrostatic field is driven via an emission from one or more radio or near field circuits of the user computing device. In another embodiment, wherein the low energy electrostatic field is driven via an emission caused in a local wireless network responsive to output from a radio circuit of the user computing device.

In an embodiment, the low energy therapeutic field includes a low energy sonic field. In an embodiment, the low energy therapeutic field includes a red or infrared illumination pattern. I another embodiment, the low energy therapeutic field includes a low energy magnetic field.

According to embodiments, the low energy therapeutic field comprises a periodic field driven as a frequency multiple of a detected cranial nerve field. In particular, the periodic field is characterized by an oscillation frequency derived from and not equal to a detected principal frequency of a brainwave. For example, the therapeutic field may be driven to have a principal frequency five to twenty hertz greater than or less than a detected brainwave frequency. For example, the therapeutic field may be driven to have a principal frequency five hertz greater than the detected brainwave frequency. In another example, the therapeutic field may be driven to have a principal frequency five hertz less than the detected brainwave frequency.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A method for applying neuro-stimulation, comprising:
receiving, into a server computer via a graphical user interface of a patient device, a condition identification corresponding to a condition experienced by a patient, wherein the condition is treatable by neuro-stimulation;
reading, into the server computer from a non-transitory computer-readable medium, a session neuro-stimulation schedule corresponding to the condition from a plurality of neuro-stimulation schedules corresponding to respective conditions;
outputting the session neuro-stimulation schedule from the server computer to the patient device; and
enabling the patient device to control a neuro-stimulation headset for applying the session neuro-stimulation schedule;
wherein enabling the patient device to control a neuro-stimulation headset for applying the session neuro-stimulation schedule includes controlling the neuro-stimulation headset to apply the session neuro-stimulation schedule to the patient;
wherein controlling the neuro-stimulation headset includes causing the neuro-stimulation headset to output an electrostatic field to the patient;
wherein controlling the neuro-stimulation headset includes controlling the neuro-stimulation headset to detect a principal frequency of a brainwave of the patient; and
wherein causing the neuro-stimulation headset to output the electrostatic field to the patient includes applying a periodic field characterized by an oscillation frequency derived from and not equal to the detected principal frequency of the brainwave of the patient.

2. The method for applying neuro-stimulation of claim 1, further comprising:
causing the patient device to display the graphical user interface; and
receiving patient input via the graphical user interface to start a neuro-stimulation session using the session neuro-stimulation schedule and
starting the neuro-stimulation session.

3. The method for applying neuro-stimulation of claim 1, further comprising:
causing the patient device to display the graphical user interface; and
receiving patient input via the graphical user interface to stop a neuro-stimulation session using the session neuro-stimulation schedule, whereupon a current neuro-stimulation session is paused or halted.

4. The method for applying neuro-stimulation of claim 1:
wherein the session neuro-stimulation schedule includes feedback setpoints for receiving feedback from the patient, via the graphical user interface, and a sensor disposed in the neuro-stimulation headset; and
wherein enabling the patient device to control the neuro-stimulation headset includes enabling the patient device to receive feedback from the patient and control neuro-stimulation output according to feedback received from the patient.

5. The method for applying neuro-stimulation of claim 4, wherein enabling the patient device to receive feedback from the patient includes enabling the patient device to receive biofeedback from the patient.

6. The method for applying neuro-stimulation of claim 1, further comprising:
  causing the patient device to display the graphical user interface including causing the patient device to display at least a "start session" graphical control object.

7. The method for applying neuro-stimulation of claim 1, further comprising:
  causing the patient device to display the graphical user interface including causing the patient device to display one or more objects for patient response during neuro-stimulation; and
  receiving feedback from the patient, wherein the patient response provides at least a portion of the feedback.

8. The method for applying neuro-stimulation of claim 7, wherein receiving feedback from the patient includes receiving biofeedback from the patient.

9. The method for applying neuro-stimulation of claim 1, further comprising:
  receiving data into the server computer corresponding to feedback from the patient during a neuro-stimulation session; and
  updating the session neuro-stimulation schedule by writing, to the non-transitory computer-readable medium, the received data, wherein writing the received data to the non-transitory computer-readable medium causes the session neuro-stimulation schedule corresponding to the condition to be modified according to the received data.

10. The method for applying neuro-stimulation of claim 9, wherein the feedback from the patient includes biofeedback from the patient.

11. The method for applying neuro-stimulation of claim 1, wherein applying a periodic field characterized by an oscillation frequency derived from and not equal to the detected principal frequency of the brainwave of the patient includes applying a periodic field having a frequency of between one and one-hundred hertz greater than or less than the detected principal frequency of the brainwave of the patient.

12. The method for applying neuro-stimulation of claim 11, wherein applying a periodic field characterized by an oscillation frequency derived from and not equal to the detected principal frequency of the brainwave of the patient includes applying a periodic field having a frequency offset, with respect to the detected principal frequency, that is determined according to a sensitivity of the patient to neuro-stimulation applied during the session neuro-stimulation schedule.

13. The method for applying neuro-stimulation of claim 1, wherein controlling the neuro-stimulation headset includes guiding the patient to arrange the headset with two emission devices of the headset positioned proximate respective selected positions on the patient's cranium.

14. The method for applying neuro-stimulation of claim 1, wherein controlling the neuro-stimulation headset to apply the session neuro-stimulation schedule to the patient causes disentrainment of patient habitual thought patterns.

* * * * *